United States Patent
Lundgren et al.

(10) Patent No.: US 10,493,258 B2
(45) Date of Patent: Dec. 3, 2019

(54) DEVICE FOR VASCULAR AND PERITONEAL ACCESS AND A DEVICE FOR HEMODIALYSIS

(71) Applicant: TRANSCUTAN AB, Södertälje (SE)

(72) Inventors: Dan Lundgren, Hovås (SE); Rickard Nyman, Uppsala (SE); Morgan Ankarbranth, Gislaved (SE)

(73) Assignee: TransCutan AB, Södertälje (SE)

( * ) Notice: Subject to any disclaimer, the term of this patent is extended or adjusted under 35 U.S.C. 154(b) by 428 days.

(21) Appl. No.: 15/124,599

(22) PCT Filed: Mar. 10, 2015

(86) PCT No.: PCT/SE2015/000014
§ 371 (c)(1),
(2) Date: Sep. 8, 2016

(87) PCT Pub. No.: WO2015/137859
PCT Pub. Date: Sep. 17, 2015

(65) Prior Publication Data
US 2017/0014612 A1    Jan. 19, 2017

(30) Foreign Application Priority Data
Mar. 11, 2014 (SE) .................................... 1400131

(51) Int. Cl.
*A61M 39/02* (2006.01)
*A61M 39/10* (2006.01)
(Continued)

(52) U.S. Cl.
CPC ........ *A61M 39/0247* (2013.01); *A61M 1/285* (2013.01); *A61M 1/3655* (2013.01);
(Continued)

(58) Field of Classification Search
CPC ...................... A61M 39/0247; A61M 5/31511; A61M 5/19; A61M 5/3145; A61M 5/3158;
(Continued)

(56) References Cited

U.S. PATENT DOCUMENTS 3,946,739 A * 3/1976 Berman .............. A61M 1/0003
604/128
4,898,669 A    2/1990 Tesio
(Continued)

FOREIGN PATENT DOCUMENTS

EP    0299547 A1    1/1989
EP    2092943 A1    8/2009
(Continued)

OTHER PUBLICATIONS

International Search Report dated Jun. 30, 2015 issued in corresponding International patent application No. PCT/SE2015/000014.
(Continued)

*Primary Examiner* — Nathan R Price
*Assistant Examiner* — Dung T Ulsh
(74) *Attorney, Agent, or Firm* — Whitmyer IP Group LLC

(57) ABSTRACT

An implantable device for venous or peritoneal access including a housing including a void having distal a proximal openings; an insert for insertion through the proximal opening comprising a venous or peritoneal catheter; a valve element mounted in a cylindrical recess of the insert; an extracorporeal coupling member of which a terminal portion can be inserted into a proximal recess of the valve element; one or two conduits extending from the catheter to the proximal end of the coupling member via the valve element and the insert for providing fluid communication, which can be interrupted by rotating the coupling member. The coupling member can be extracted from the recess only in a state of interrupted communication.

21 Claims, 7 Drawing Sheets

(51) Int. Cl.
*A61M 39/26* (2006.01)
*A61M 1/28* (2006.01)
*A61M 1/36* (2006.01)
*A61M 5/14* (2006.01)

(52) U.S. Cl.
CPC ............ *A61M 1/3661* (2014.02); *A61M 5/14* (2013.01); *A61M 39/02* (2013.01); *A61M 39/105* (2013.01); *A61M 39/26* (2013.01); *A61M 1/3653* (2013.01); *A61M 2039/027* (2013.01); *A61M 2039/0255* (2013.01); *A61M 2039/0258* (2013.01); *A61M 2039/0264* (2013.01); *A61M 2039/0273* (2013.01); *A61M 2039/0276* (2013.01); *A61M 2039/0282* (2013.01); *A61M 2039/1033* (2013.01)

(58) Field of Classification Search
CPC ............ A61M 5/36; A61M 2039/0229; A61M 2039/027; A61M 2039/0273
See application file for complete search history.

(56) References Cited

U.S. PATENT DOCUMENTS

| | | | |
|---|---|---|---|
| 4,983,162 A * | 1/1991 | Metais | A61M 39/0247 137/614.17 |
| 7,708,722 B2 | 5/2010 | Glenn | |
| 7,772,314 B2 | 8/2010 | Fernihough et al. | |
| 7,846,139 B2 | 12/2010 | Zinn et al. | |
| 8,079,987 B2 | 12/2011 | Moorehead et al. | |
| 8,282,610 B1 | 10/2012 | Glenn | |
| 2004/0249361 A1 * | 12/2004 | Denoth | A61F 2/0077 604/523 |
| 2006/0047249 A1 | 3/2006 | Shubayev et al. | |
| 2008/0114308 A1 * | 5/2008 | di Palma | A61M 39/0208 604/246 |
| 2009/0182285 A1 * | 7/2009 | Lee | A61M 1/0009 604/228 |
| 2010/0268165 A1 * | 10/2010 | Maniar | A61M 39/0208 604/175 |
| 2012/0116316 A1 | 5/2012 | Schutz et al. | |
| 2013/0237781 A1 * | 9/2013 | Gyrn | A61M 5/14248 600/309 |
| 2016/0067470 A1 * | 3/2016 | Silva Pires e Albuquerque | A61M 39/0247 604/500 |

FOREIGN PATENT DOCUMENTS

| | | |
|---|---|---|
| WO | WO 92/13590 | 8/1992 |
| WO | WO 92/21403 | 12/1992 |
| WO | WO 99/20338 | 4/1999 |
| WO | WO 2009/002839 A1 | 12/2008 |

OTHER PUBLICATIONS

Extended European Search Report Application No. 15761595.6 dated Apr. 9, 2018; Completed: Mar. 22, 2018 8 pages.

* cited by examiner

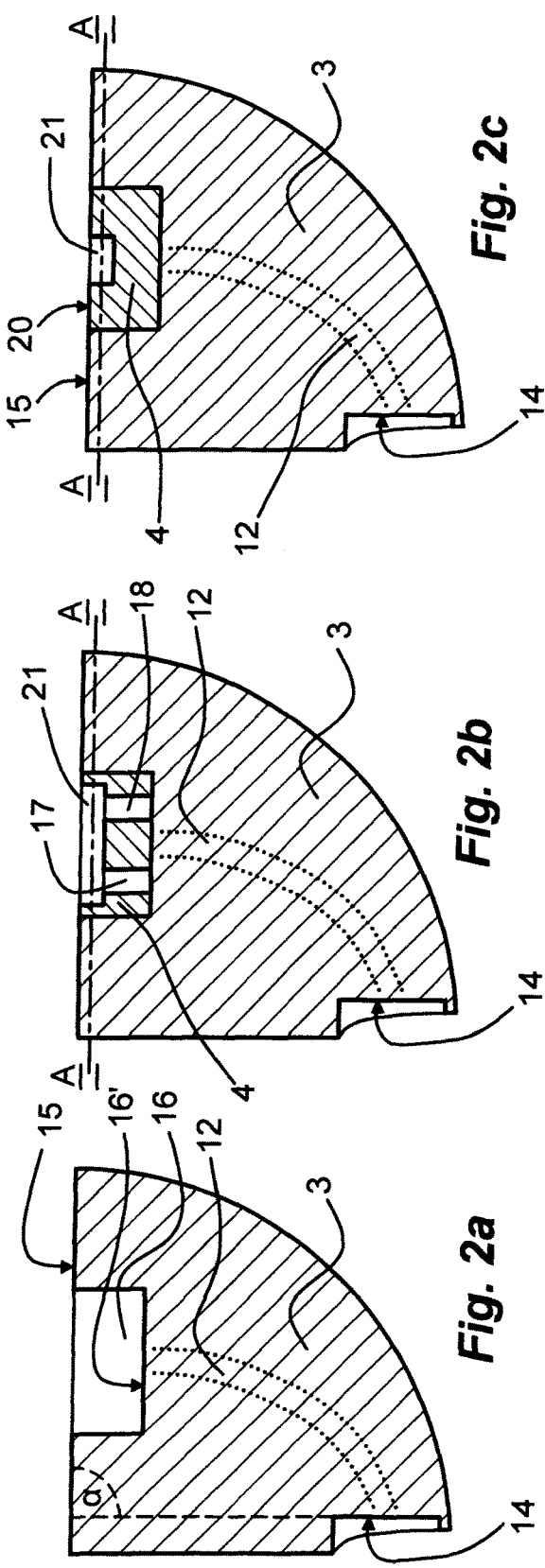
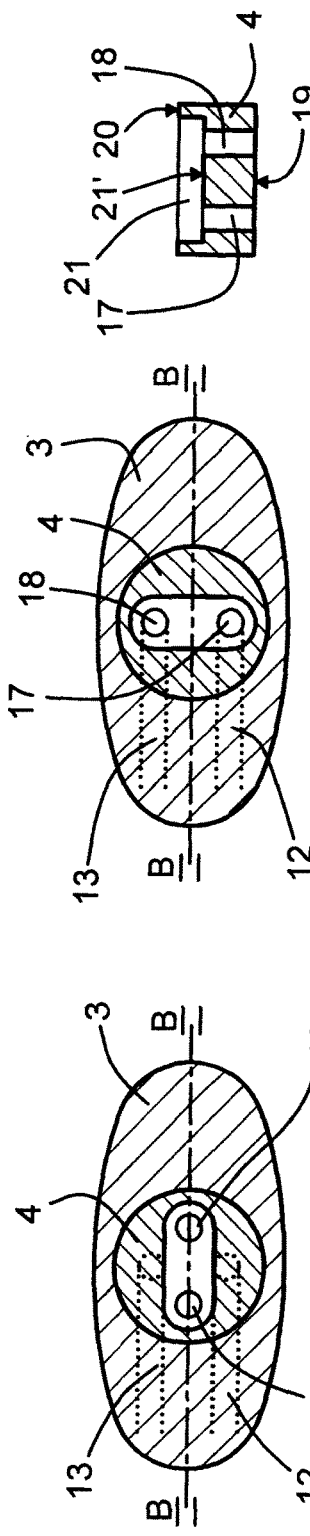
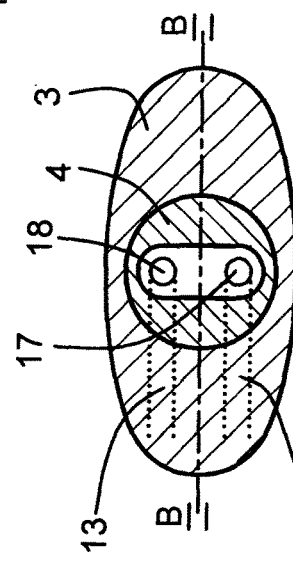
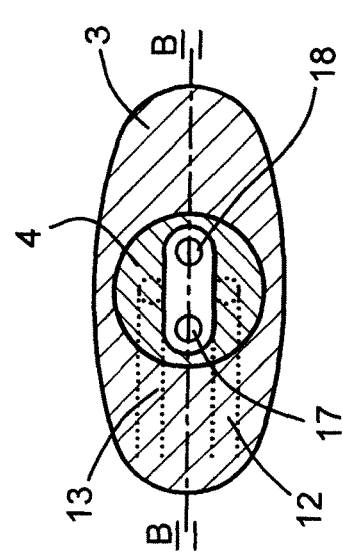

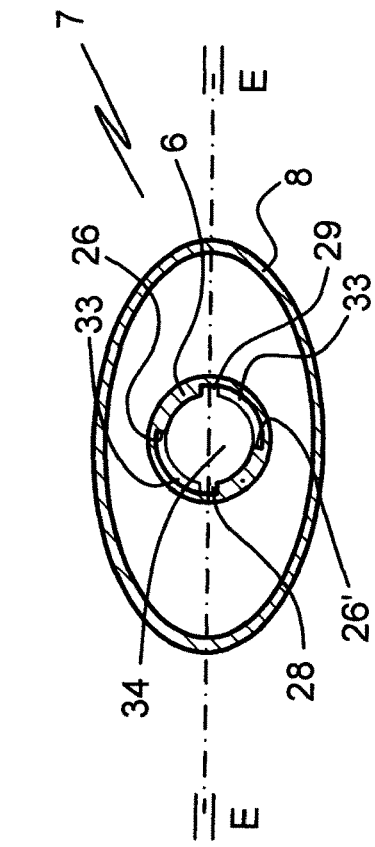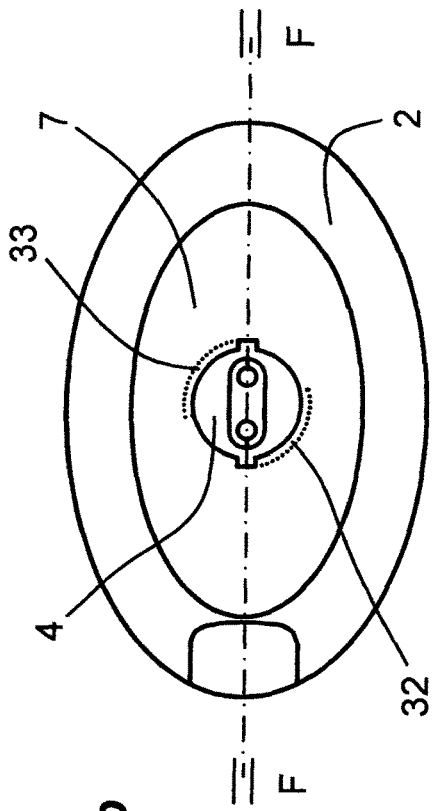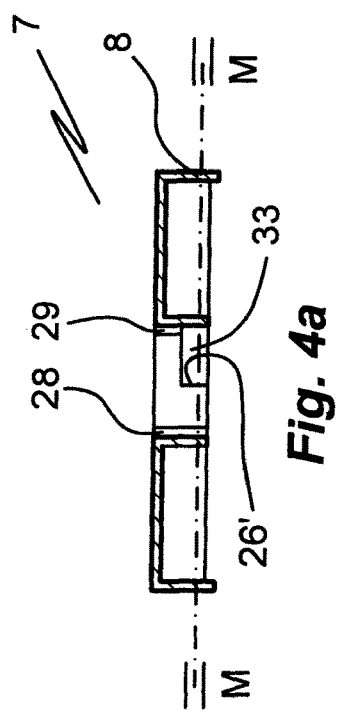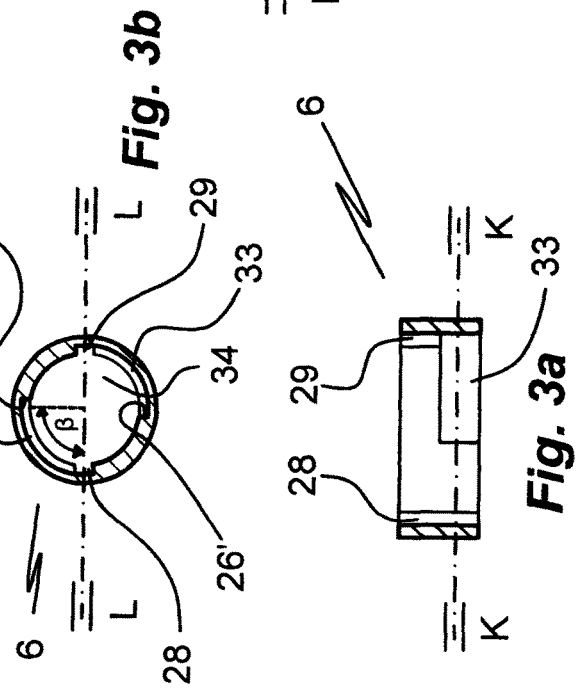

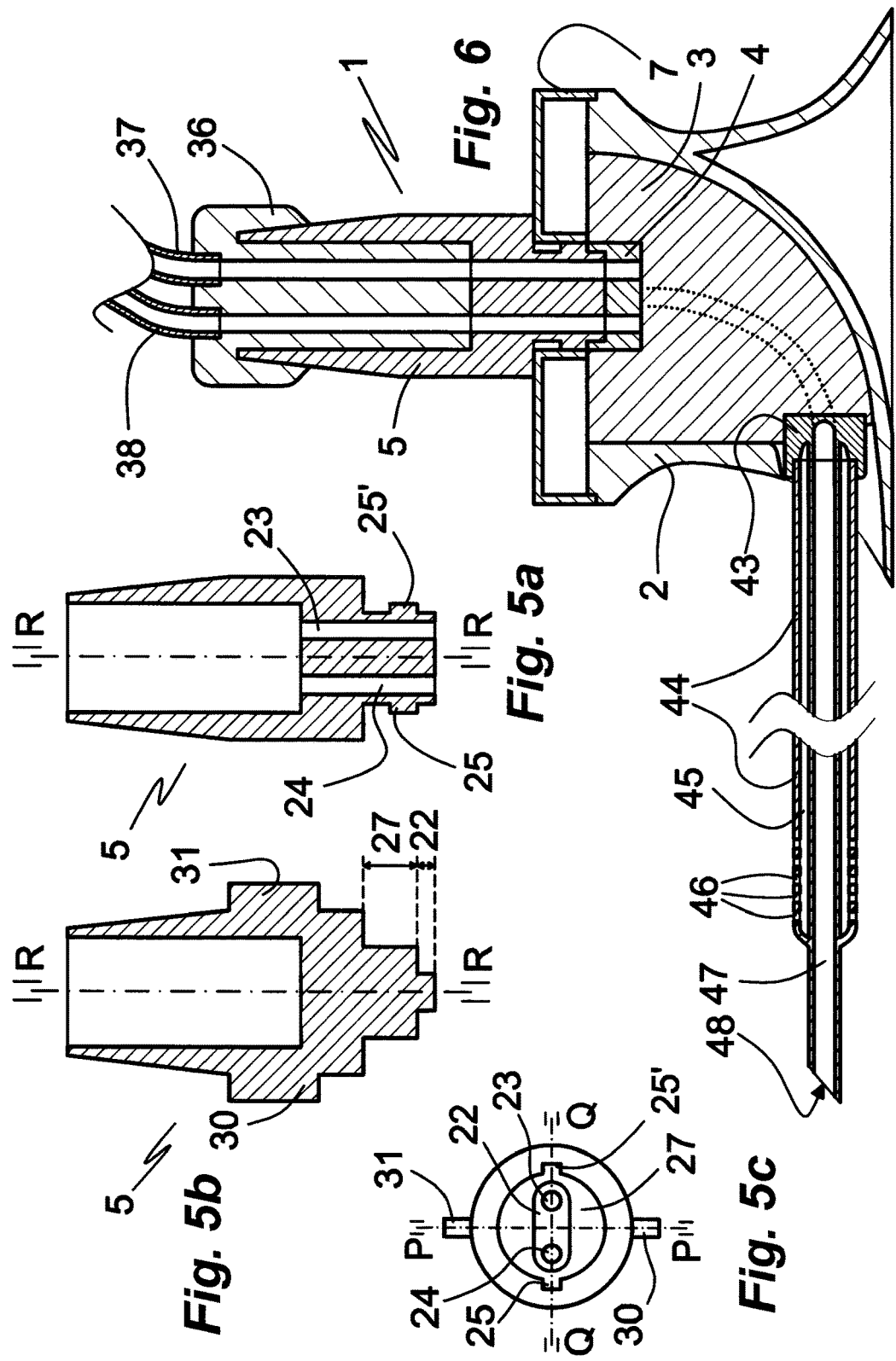

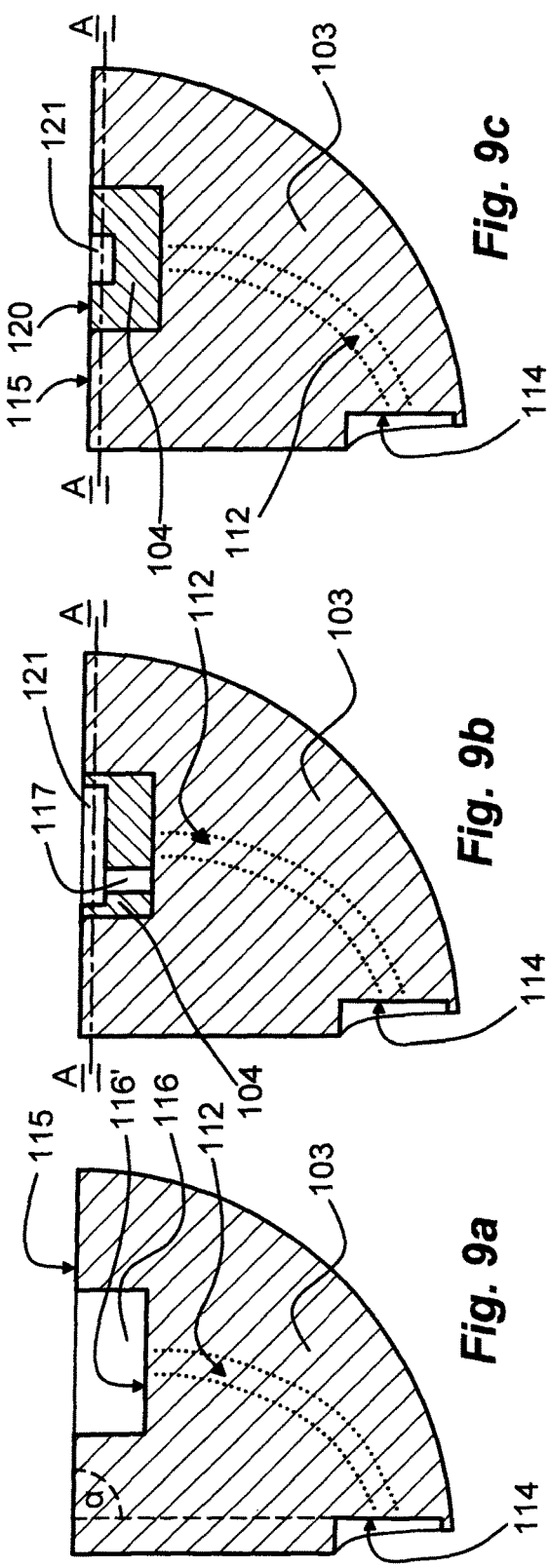

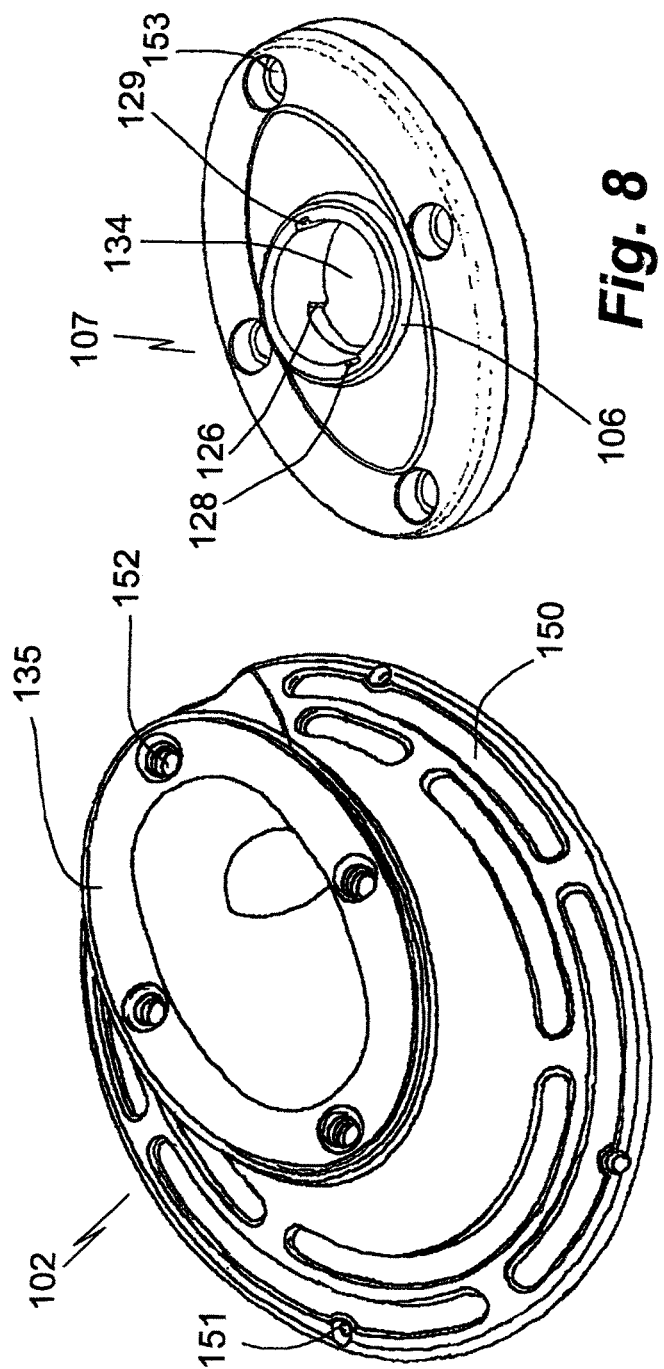

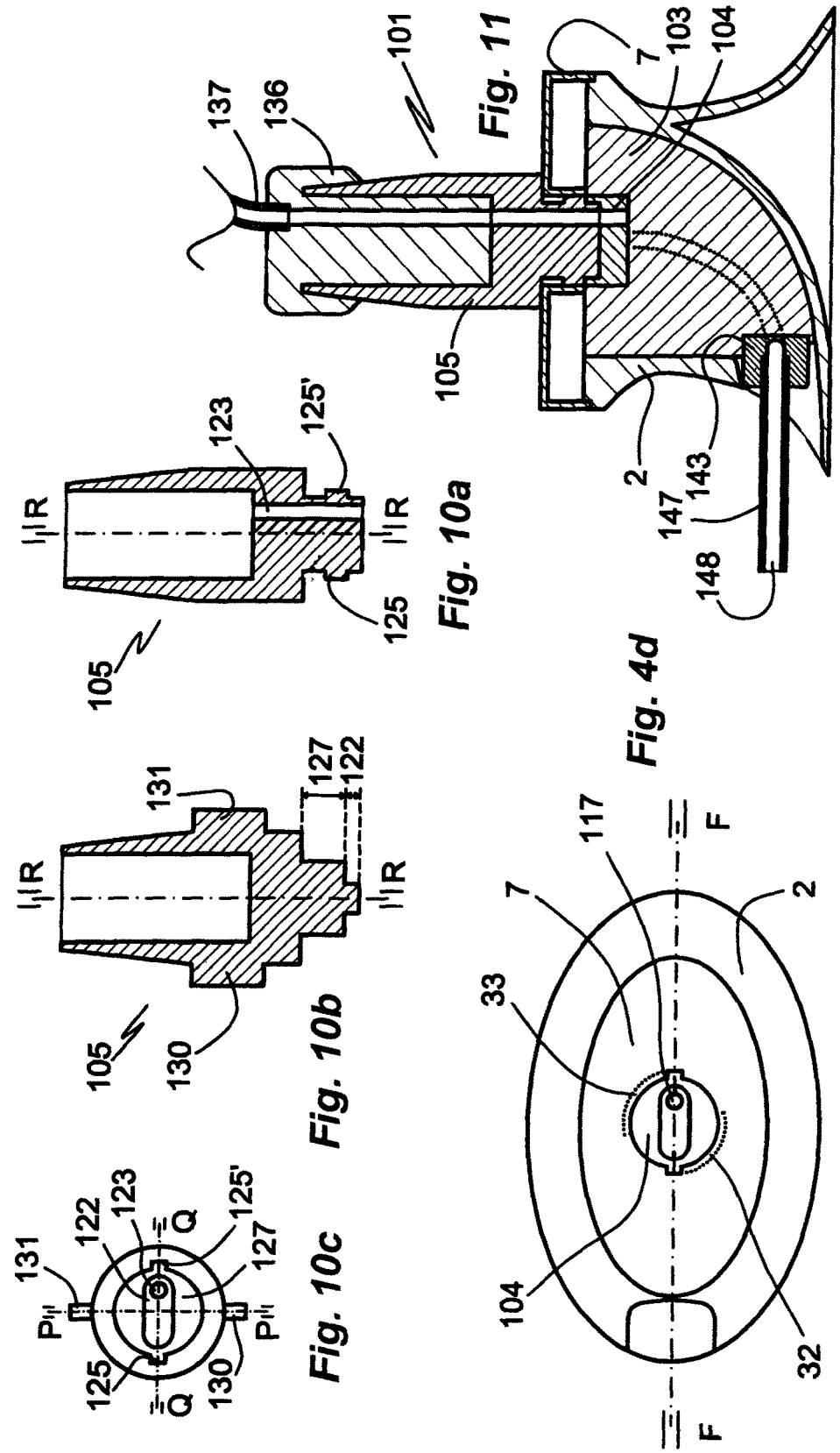

DEVICE FOR VASCULAR AND PERITONEAL ACCESS AND A DEVICE FOR HEMODIALYSIS

CROSS REFERENCE TO RELATED APPLICATIONS

The present application is a 35 U.S.C. § 371 National Phase conversion of PCT/SE2015/000014, filed Mar. 10, 2015, which claims benefit of Swedish Application No. 1400131-7, filed Mar. 11, 2014, the disclosures of which are incorporated herein by reference. The PCT International Application was published in the English language.

FIELD OF THE INVENTION

The present invention relates to a device for vascular access, in particular venous access, such as for hemodialysis, and to a device for peritoneal access.

BACKGROUND OF THE INVENTION

Patients with end stage kidney failures who do not receive a kidney transplant must undergo either hemodialysis (HD) or peritoneal dialysis (PD). In hemodialysis waste products and extra fluid is removed by a special kind of filter. A vascular access is needed to withdraw the blood and to return it in a purified state to the patient. In peritoneal dialysis a dialysis solution is infused into the abdomen by means of a catheter. In the dialysis solution wastes and extra fluid from blood are accumulating and then withdraw by draining the dialysis solution.

For both dialysis modalities the requirement of a chronic intra-corporeal access poses a challenge and is associated with a high level of morbidity.

In peritoneal dialysis a standard catheter is used. The catheter has polyester cuffs which merge with scar tissue to keep it in place. Since the catheter is sticking out from the skin between dialysis sessions it is frequently displaced, which increases the risk of wound irritation and infection.

Three access methods are available in hemodialysis: a) arteriovenous fistula (AV fistula); b) arteriovenous graft (AV graft); and c) venous catheter (VC). In the preferred method the provision of an AV fistula requires long-term planning, since a usable fistula only develops over time; in rare cases the development may take as long as two years. On the other hand, a properly formed fistula is less likely than other kinds of AV access to form blood clots or become infected. About 70% of all dialysis patients end up with an AV fistula. If the patient has small veins that won't properly develop into a fistula, a vascular access that connects an artery to a vein using a synthetic tube or graft can be inserted under the skin. Compared with properly formed fistulas grafts tend to have more clotting and infection problems. The need to be replaced sooner and more sparsely used than fistulae.

If kidney disease is progressing quickly there may not be time enough to get a permanent vascular access before dialysis must be started. It may then be necessary to use a venous catheter as a temporary access. The catheter is inserted in to a vein in the neck, chest, or leg near the groin. The catheter has two chambers or conduits to allow blood from in two directions, to and from the vein. Once a catheter has been placed insertion of a needle is no longer required. However, catheters are not ideal for permanent access. The can clog, become infects, and cause narrowing and irritation of the veins in which they are placed.

Despite the aforementioned problems with permanent catheters about 20%-30% of all hemodialysis patients end up with them as chronic access. FDA's Annual Registry Report for 2009 states that "Despite ongoing initiatives to reduce catheter use . . . the use of catheters has remained at 17-18 percent since 2003".

Similarly to the PD catheter the frequent movement of the access tube induces an increased risk of infection and wound irritation. Another risk for bacterial or mold infection is constituted by the use of access ports comprising membranes for injection/withdrawal of fluid. Therefore membranes intended for penetration by a hypodermic needle or similar should be avoided in permanently attached/tissue integrated venous access ports.

In view of the foregoing the provision of an improved device for permanent vascular access for hemodialysis is highly desirable.

Also desirable is the provision of an improved device for single lumen permanent vascular access, such as for repeated infusion into the blood stream, in particular infusion of solutions or suspensions of nutrients, pharmaceuticals, vitamins, and salts.

Devices for permanent venous access, such as the ones disclosed in WO 92/21403 A, WO 92/13590 A, WO 99/20338 A, WO 2009/002839 A1, U.S. Pat. No. 7,708,722 B2, U.S. Pat. No. 7,846,139 B2, U.S. Pat. No. 7,772,314 B2, U.S. Pat. No. 8,079,987 B2, and U.S. Pat. No. 8,282,610 B2, are known in the art.

Furthermore it is desirable to provide an improved device for peritoneal access, such as for peritoneal dialysis or for administration of drugs to a patient via the peritoneum, for instance administration of insulin to Type I diabetics who do no well respond to subcutaneous insulin.

Objects of the Invention

It is an object of the invention to provide a device for permanent vascular, in particular venous, or peritoneal access which comprises one or more of the following features:

being permanently attachable to a patient by surgery so as to be disposed in part intra-corporeally, in part extra-corporeally;

comprising materials and surfaces designed for tissue integration;

allowing a vascular, in particular venous, access portion thereof, such as a venous catheter, or a peritoneal access portion such as a peritoneal catheter, thereof to be easily exchanged without the need of dismounting the housing of the device;

allowing a venous or peritoneal access portion thereof, such as a venous or peritoneal catheter, to be easily inserted into a vein, in particular into a deep-lying vein which is not easily visually located, or to be inserted into the peritoneum;

allowing establishing easily and safely fluid connection with a dialysis apparatus or other blood treatment apparatus, or for non-dialysis application, in particular infusion of aqueous solutions or suspensions of pharmaceuticals, nutrients, salts and vitamins;

posing a low risk of infection and irritation to the patient by, i.a., avoiding the use of membrane(s) designed for penetration by hypodermic needles or similar;

allowing exchange of the venous or peritoneal access portion of the device comprising the catheter when clogged for a new venous or peritoneal access portion.

SUMMARY OF THE INVENTION

According to the present invention is provided a device for permanent venous access, such as for hemodialysis. Also provided is a device for permanent peritoneal access.

The device of the invention may, of course also be used for providing venous access for methods other than hemodialysis such as, for instance, frequent and long-term administration of large volumes of aqueous solutions or suspensions of pharmaceuticals, nutrients, vitamins and salts.

Permanent access is obtained by attaching the device to the patient by surgery followed by tissue integration of appropriately designed biocompatible surfaces thereof. The surfaces to be integrated are comprised by a housing comprising a void. Thus, it is the housing of the device which is attached to the body of a person by surgery, so that a distal portion of it is located in soft tissue, whereas a proximal portion is extending from the skin surface.

The device comprises or is attachable to a venous catheter or a peritoneal catheter. In one embodiment the venous catheter is a double lumen catheter allowing simultaneous upstream withdrawal of blood from a vein and downstream infusion of purified blood into the same vein. In another embodiment, the venous catheter or peritoneal catheter is single lumen catheter allowing infusion of aqueous solutions or suspensions of pharmaceuticals, nutrients, vitamins, salts etc. into the blood stream or the peritoneum.

In correspondence with the design for use with a single-lumen or double-lumen venous catheter the device comprises one or two conduits extending from the catheter to an extracorporeal portion of the device, at which the conduit or each conduit is connected to a flexible tube. At their other ends the flexible tube(s) is/are connected to an apparatus for hemodialysis, to a container with infusion fluid, and the like. Each of the conduits comprises three severable portions disposed in corresponding elements of the device The device of the invention comprises a housing. The housing preferably comprises a mantle in the form of a skirt comprising about elliptical upper and lower edges disposed in about parallel planes. The housing is designed for implantation into soft tissue. It is preferably of a metal or other material capable of integration with the soft tissue to which it is implanted. The housing is not fully implanted in the tissue but only partially, so that a lower portion thereof is surrounded by the tissue whereas an upper portion thereof extending through the skin is disposed exteriorly of the tissue. The void comprises two openings, one disposed exteriorly of the tissue and one disposed in the tissue. The rims of the openings define planes, of which, in an implanted state, the plane of the exterior opening is about parallel with the skin surface whereas the plane of the interior opening is about perpendicular to it.

The device for venous or peritoneal access of the invention further comprises an insert disposable in the void and removable from it. In an implanted state of the housing the insert can be inserted into the void through the exterior opening. When fully inserted the insert closes the interior opening of the void. The insert comprises one or two insert conduits extending from a first, optionally flat, face thereof disposed intra-corporeally at the interior opening of the housing to a flat bottom face of an insert recess in a second face thereof disposed extra-corporeally, the first and second faces including an angle $\alpha$ of about 90°, such as an angle of from 80° or 85° or 88° to 100° or 95° or 92°, respectively.

The device for venous or peritoneal access of the invention further comprises a cylindrical valve member, preferably of about same diameter and height as the insert recess. The valve member is disposed in the insert recess and comprises one or two valve member conduits extending between its distal end face and the bottom face of an oblong radially extending valve member recess in a proximal face thereof. The valve member conduits are equidistant with the openings of the insert conduits at the bottom face of the insert recess. Preferably they are equally spaced from the center of the recess which corresponds to the center of the valve member, in particular equally spaced on a diameter thereof. In the single-conduit design the valve member conduit and the opening of the insert conduit are disposed at the same distance from the center of the insert recess/the center of the valve member. Preferably the valve member has a diameter slightly smaller than the diameter of the recess to make it snugly fit into the recess and rotatable in the recess.

The device for venous or peritoneal access of the invention further comprises a coupling member. The coupling member has a distal and a proximal end. It comprises a coupling portion extending from its distal end in a proximal direction of preferably same but positive form as the valve member recess. The coupling portion can be inserted into the valve member recess and withdrawn from it. The coupling member further comprises one coupling member conduit or two coupling member conduits generally disposed in parallel. In the one-conduit design the distal opening of the coupling member conduit, in an inserted position of the coupling member into the valve member recess, is equidistant with the proximal opening of the valve conduit from the central axis of the valve member and extends from the distal end of the coupling member towards its proximal end.

The coupling member conduit(s) extend from the distal face of the coupling member to a proximal portion of the coupling member. The coupling member conduit(s) are so disposed that, in an inserted position, that is, in a position when the coupling portion is inserted in to the oblong recess of the valve member, the coupling member conduit(s) are in line with the valve member conduit(s). The valve member is displaceable from an open position to a closed position or vice versa by rotation of the coupling member so that the valve member conduit(s) is/are displaced from an open in-line position to a closed off-line position. Said open position provides for fluid communication through the one insert conduit/valve member conduit/coupling member conduit or the pair of such conduits.

It is preferred for the insert to comprise coupling means disposed at its first face for coupling with a double lumen venous catheter so as to establish communication of the catheter conduits with the insert conduits.

According to first preferred aspects of the invention the insert comprises a single or double lumen catheter firmly attached at the first face of the insert in a manner to establish fluid communication between the conduit(s) of the catheter and the insert conduit(s). The catheter is selected from single or double lumen venous access catheter and single lumen peritoneal access catheter.

According to a second preferred aspect of the invention the device comprises a means for restricting the rotation of the coupling member, the means comprising or preferably consisting of a rotation restricting element. It is preferred for rotation to be restricted to an angle $\beta$ of about 90°, such as an angle of from 80° to 100°.

According to a third preferred aspect of the invention the rotation restricting element comprises one or more shoulders disposed in distal sections of the central bore of the rotation restricting element, the shoulders co-operating with one or more radially extending lugs disposed on a cylindrical portion of the coupling member.

According to a fourth preferred aspect the device of the invention comprises a means for controlling the insertion of the coupling member into the valve member recess so as to only permit insertion or withdrawal at a closed position of the valve member. The insertion control means is preferably comprised by the rotation restricting element.

According to a fifth preferred aspect of the invention the insertion control means comprises one or more groves extending axially in the wall of the central bore. The groove(s) are capable of co-operation with the lug(s) of the coupling member. Full insertion of the coupling member into the central bore of the rotation restricting element is only possible when the valve member is in a closed position. The cylindrical section carrying the lugs extends preferably from the distal terminal section in a proximal direction.

According to a further preferred aspect of the invention the rotation restricting element is comprised by a cover which can be mounted on and dismounted from a proximal extracorporeal face of the housing, which is preferably coplanar with the second face of the insert.

According to a still further preferred aspect of the invention the cover comprises a shield and a mounting member into which the rotation restricting element is integrated. The shield is preferably attachable to the mounting member upon mounting the mounting member on the housing.

According to the invention is furthermore disclosed a preferred embodiment of the access device for hemodialysis of the aforementioned kind, comprising:
 a housing comprising a void having a distal opening and a proximal opening;
 a venous double lumen catheter comprising a mounting insert at its proximal end;
 a cylindrical valve element mountable in a cylindrical recess of the mounting insert;
wherein, upon implantation of the housing, the distal opening is disposed so as to face soft tissue of the patient whereas the proximal opening is disposed exteriorly of the patient, and wherein the mounting insert of the double lumen catheter is mountable in the housing by inserting the venous double lumen catheter foremost into the proximal opening and then making the venous catheter pass through the distal opening.

According to a preferred aspect of the invention the cylindrical recess in the mounting insert for mounting the valve element is disposed in a distal face thereof exteriorly of the patient's body.

According to another preferred aspect of the invention the mounting insert is mounted in a cylindrical recess disposed in a distal face of the mounting insert.

According to still another preferred aspect of the invention a first conduit of the insert provides fluid communication with a first lumen of the double lumen venous catheter and a second conduit of the insert provides fluid communication with a second lumen of the double lumen venous catheter. It is furthermore preferred for the distal openings of said first and second conduits to open at the bottom face of the cylindrical recess.

The access device preferably comprises an extracorporeal coupling member, the coupling member comprises a distal terminal portion mountable in a non-cylindrical, for instance oblong, recess in the proximal face of the valve element, the coupling member comprising a first and a second conduit designed to be brought, in a coupled position, into fluid communication with the respective conduits of the valve element at their distal openings disposed in said second recess.

It is preferred for the coupling member to be dismountable in a closed valve position only. It is preferred for the device to comprise a means for restricting the rotation of the coupling member, the means comprising or consisting of a rotation restricting element such as a shoulder or flange designed for co-operation with one or more lugs extending radially from a cylindrical portion of the coupling member. In particular, it is preferred for the insertion control means to comprise one or more groves extending axially in the wall of a central bore of a rotation restricting element comprised by the device. The groove(s) are capable of co-operation with the lug(s) of the coupling member. Full insertion of the coupling member into said central bore of the rotation restricting element is only possible when the valve member is in a closed position. The cylindrical portion carrying the lugs extends preferably from the distal terminal section in a proximal direction.

According to a further preferred aspect of the invention the rotation restricting element is comprised by a cover which can be mounted on and dismounted from a proximal extracorporeal face of the housing, which is preferably coplanar with the second face of the insert.

According to a still further preferred aspect of the invention the cover comprises a shield and a mounting member into which the rotation restricting element is integrated. The shield is preferably attachable to the mounting member upon mounting the mounting member on the housing.

In the following the invention will be explained in more detail by reference to two preferred embodiments illustrated in a drawing.

SHORT DESCRIPTION OF THE FIGURES

FIGS. 1b, 2a-2f, 4c, 5a-5c, and 6 relate to a first embodiment of the device of the invention. FIGS. 1c, 4d, 9a-9f, 10a-10c, and 11 relate to a second embodiment of the device of invention. FIGS. 1a, 1d, 3a, 3b, 4a, 4b, 5d are shared by the first and second embodiments of the device of the invention. FIGS. 7 and 8 pertain to a variety of the housing of the first and second embodiments. In particular:
 FIGS. 1a-1c illustrate a housing, in section C-C (FIG. 1a), in a front view (FIGS. 1b and 1c) and in a top view (FIG. 1d);
 FIGS. 2a-2e and 9a-9e illustrate alternative inserts:
 Section B-B (FIGS. 2a, 9a);
 Section B-B, with a valve member mounted in a closed condition (FIGS. 2b, 9b);
 Section B-B, with a valve member mounted in an open condition (FIGS. 2c, 9c);
 Section A-A, with a valve member mounted in a closed condition (FIGS. 2d, 9d);
 Section A-A, with a valve member mounted in an open condition (FIGS. 2e, 9e);
 FIGS. 2f and 9f illustrate alternative valve members, in the same axial section as in FIGS. 2b, 9b;
 FIGS. 3a and 3b illustrate a locking element, in section L-L (FIG. 3a) and in section K-K (FIG. 3b);
 FIGS. 4a, 4b illustrate a cover with integrated locking element, in section E-E (FIG. 4a) and in section M-M (FIG. 4b); FIGS. 4c and 4d are top views of the cover mounted on the housing comprising the insert with the valve element of FIGS. 2f and 9f, respectively;

FIGS. 5a-5c, 9a-9c illustrate a coupling member, in axial sections Q-Q (FIGS. 5a, 10a) and P-P (FIGS. 5b, 10b), and in a bottom view (FIGS. 5c, 10c);

FIGS. 6, 11 illustrate the device of the invention, complete with a double lumen and single lumen venous catheter, respectively and inlet/outlet tubes for connection with a dialysis apparatus, peritoneal dialysis solution reservoir or similar, in a closed condition and in a proximal/distal section corresponding to section F-F in FIGS. 4c, 4d;

FIGS. 7, 8 are perspective views of a variety of a housing of the invention.

DESCRIPTION OF PREFERRED EMBODIMENTS

Example 1

First Embodiment of the Device of the Invention

Figure 1D:
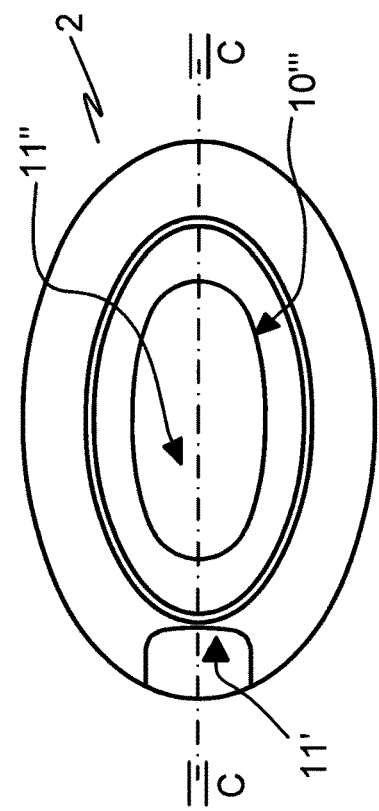
Figure 1C:
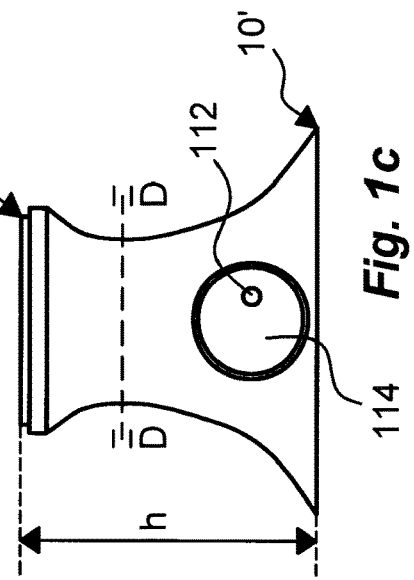
Figure 1A:
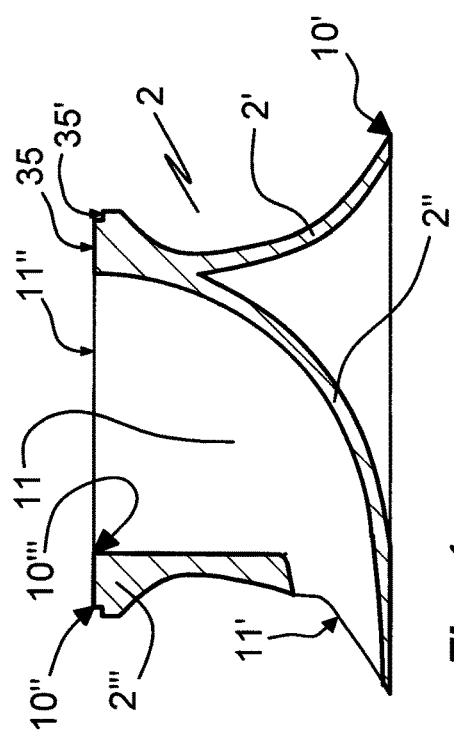
Figure 1B:
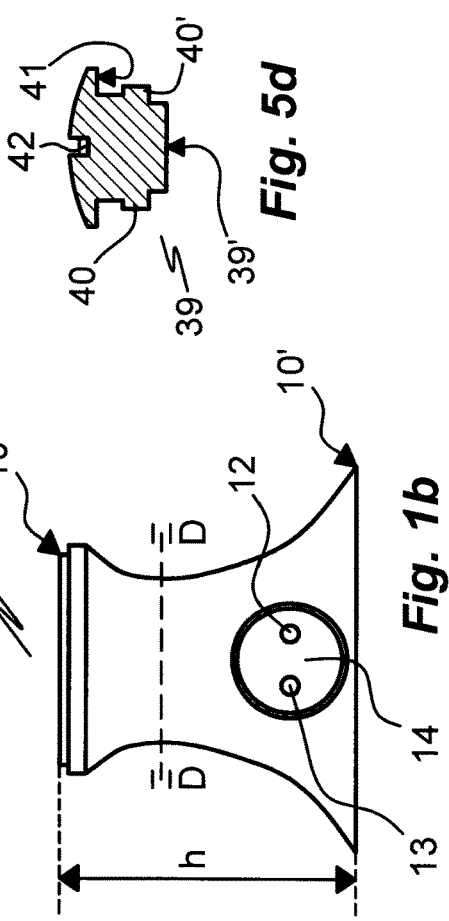

A first embodiment 1 of the venous access device of the invention relates to a device for hemodialysis (FIG. 6). The device 1 comprises a housing 2, an insert 3 disposed in a void 11 of the housing 2, and a cylindrical valve member 4 disposed in a cylindrical recess 16 of the insert. The housing 2 has about the form of a skirt 2', which is about elliptical in radial section or a top view (FIG. 1d). The housing 2 extends between about elliptical upper 10" (proximal) and lower 10' (distal) circumferential rims disposed in parallel planes (FIG. 1b). Broken line D-D indicates roughly the extra-corporeal/intra-corporeal border. The interior of the housing 2 defined by the skirt 2' and said planes is divided by an insert holding wall 2" which, together with sections of the skirt 2' (inner face of 2'''), defines the void 11 in which the insert 3 is disposed. The wall thickness of an elliptic upper/proximal portion 2''' of the skirt 2' extending downwards from the upper rim 10" over about a fourth to a third of the proximal/distal height h of the skirt 2' is substantially greater than the thickness of the major part of the skirt 2'. The increased wall thickness allows the provision of threaded bores (not shown) in a proximal face 35 of the housing 2 which extends inwardly from the upper rim 10" for the rugged mounting of a cover 7.

In an inserted position the insert 3 is substantially symmetric in respect of a plane (C-C, FIG. 1d) defined by the long axes of the upper and lower skirt rim 10", 10' ellipsis. In a side view the insert 3 has the general form of a circular segment of about 90°. The insert holding wall 2" extends from one end of the long axis of the elliptical proximal (upper) skirt rim 10" to near the opposite end of the long axis of the elliptical distal (lower) skirt rim 10'. The insert wall 2" is about U-formed in a transverse vertical (proximal/distal) section, viz. in a distal/proximal section coinciding with or parallel with the short axes of the upper and lower skirts 10", 10'. The form of the void 11 corresponds closely to the form of the side and bottom walls of the insert 3. Upon insertion into the void 11 the side/bottom walls of the insert 3 abut snugly corresponding wall sections of the housing 2. The void 11 has a proximal (upper) opening 11" defined by a proximal inner circumferential edge 10''' of the housing 2 and distal (lower) opening 11' centered in respect of the long axis of the lower skirt rim 10'. The distal opening 11' is disposed near the end of the elliptic lower skirt axis opposite to the end of the long axis of the elliptical proximal inner circumferential rim 10''' from which the insert holding wall 2" extends in a skew downward direction. The housing 2 is shown in FIGS. 1a, 1c in a longitudinal distal/proximal section (FIG. 1a) and in a top view (FIG. 1c). In FIG. 1b the housing 2 with the insert 3 disposed in the void 11 is shown in a frontal view displaying the first opening 11', in which a distal face 14 of the insert 3 and the distal openings of its conduits 12, 13 are seen. The broken line D-D indicates the level of the intra-corporeal (distal)/extracorporeal (proximal) border. The portion of the housing 2 located downwards (distally) of D-D (skin level) thus is disposed in soft tissue.

In FIGS. 2a-2c the insert 3 is shown in a vertical sectional view B-B. In a horizontal section A-A (FIGS. 2d, 2e) the insert 3 is of about elliptic form. FIGS. 2b-2e illustrate the insert 3 with a valve member 4 mounted in a proximal recess 16 thereof. The insert 3 is substantially symmetric in respect of a plane B-B dissecting it in a proximal/distal direction, which plane is identical with the plane C-C (FIG. 1d) of the housing 2. The insert 3 comprises two faces, said distal face 14 and a proximal face 15. In a mounted position of the insert 3 the proximal face 15 is coplanar with an upper, proximal face 35 of the housing 2, that is, is disposed in the second opening 15 of the housing 2, whereas its distal face 14 is disposed at the inner end of the first opening 11' of the housing 2. The generally flat faces 14, 15 are disposed in planes or defined by planes dissecting each other by an axis perpendicular to the plane B-B. The first and second faces 14, 15 include an angle α of about 90°.

The insert recess 16 is of cylindrical form. Parallel conduits 12, 13 of equal length extend from the distal face 14 of the insert to the bottom face 16' of the insert recess 16. The valve member 4 mounted in the insert recess 16 is also of cylindrical form and of same size as the recess 16. The valve member 4 has flat lower 19 (distal) and upper 20 (proximal) faces. The upper (proximal) face 19 of the valve member 4 comprises an oblong recess 21. Two parallel conduits 17, 18 extend between the distal face 19 and the bottom face 21' of the valve member recess 21. The openings of conduits 12, 13 at the bottom face 16' of the insert recess 16 and the distal face 19 openings of the valve member conduits 17, 18 are equally spaced. When the valve member 4 is inserted in the insert recess 16 the proximal face 20 of the valve member 4 is coplanar with the proximal face 15 of the insert 3.

The insert 3 is held in place by the mounting frame 8 of a cover 7 shown in sectional side (E-E) and bottom (M-M) views in FIGS. 4a, 4b. The cover 7 is mounted on the upper (proximal) face 15 of the housing 2 by means of screws (not shown), and is supported by a circumferential shoulder 35' of the housing 2. In a top view (FIG. 4c) the cover 7 is shown mounted on the housing 2, its circumference being of substantially same form and size as the upper rim 10" of the housing 2. The cover 7 comprises a rotation restricting element 6 of cylindrical form with central bore 34. The cover 7 with the rotation restricting element 6 is mounted on the housing 2 so that the common axis of the rotation restricting element 6 and its central bore 34 coincide with the cylinder axis of the valve member 4. By the diameter of the central bore 34 being somewhat smaller than the diameter of the valve member 4 the latter is locked in the insert recess 16.

A venous double lumen catheter 43, 44 is mounted at the distal face 14 of the insert 2. The catheter 43, 44 protrudes through the distal opening 11' of the housing 2 and extends from the housing 2 in a direction about parallel with the lower rim 10' of the skirt 2". At its proximal end, which abuts the distal face 14 of the insert 3, the catheter 43, 44 comprises a cylindrical base 43, the proximal face of which is mounted on the distal face 14 of the insert 3. The base 43 comprises first and second conduits, which are in fluid communication with the conduits 12, 13 of the insert 3. From the other face of the base 43 protrudes a flexible double conduit catheter tube 44 comprising outer 45 and inner 47 conduits. Near its distal end the outer conduit 45 is provided with a number of radial inlet orifices 46. The inner conduit 47 extends for a further distance and comprises a single orifice 48 at its distal end. The venous catheter 43, 44 is inserted into a major vein (not shown) in a manner that the orifices 46 of its outer conduit 45 are disposed upstream of the orifice 48 of its inner conduit 47. The insert 3 with the venous catheter 43, 44 can be inserted into the void 11 of the housing 2 through the proximal opening 11", the catheter 43, 44 passing during insertion through the distal opening 11' of the housing 2 from where it is inserted into soft tissue and, finally, into a vein (not shown). In a corresponding manner the catheter 43, 44 and the insert 3 can be removed from the vein/soft tissue/void 11.

The valve formed by the combination of insert recess 16 and valve member 4 can be opened and closed by rotation of the valve member 4. In an open position the conduits 17, 18 of the valve member 4 are in communication with the conduits 12, 13 of the insert 2, that is, their facing openings are in a superimposed position. From this open position the valve 4, 16 is brought to a closed position by rotating the valve member 4 by about 90°. Rotation is accomplished by inserting an oblong rotation means into the oblong valve member recess 21 and turning the rotation means over a desired angle. A suitable rotation means is provided by two alternatively used tools, a coupling member 5 and a protecting cap 39.

The coupling member 5 is used for providing fluid communication between the conduits 17, 18 of the valve member 4 and a dialysis apparatus or similar.

Figure 5D:
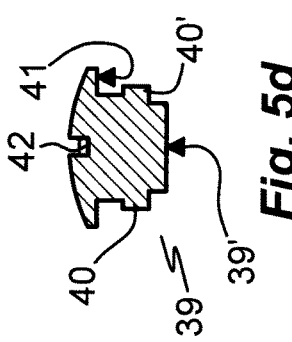
FIG. 5d illustrates a rotationally symmetric protection cap in axial section, for which the coupling member is exchanged during non-use of the device.

Fluid communication between a vein and a dialysis apparatus or similar device is so provided by means of the intermediate access device 1, specifically via the conduits of the venous catheter 43, 44, the insert 2, the valve member 4, the coupling member 5 and flexible tubes connecting the coupling member 5 with the apparatus. The coupling member 5 comprises conduits 23, 24 extending in an axial direction from its distal end to its proximal end. At their distal openings the coupling member conduits 23, 24 are equidistant with the valve conduits 17, 18. The coupling member 5 is rotationally symmetric by a two-fold symmetry in respect of a central axis R-R (FIGS. 5*a*, 5*b*) corresponding to the intersection of planes P-P and Q-Q in FIG. 5*c*. The coupling member 5 is provided with a valve operating portion 22 extending from its distal end and of same but positive form as the valve member recess 21. Upon insertion of the valve operating portion 22 into the valve member recess 21 (FIG. 6) the valve member 4 can be rotated by rotating the coupling member 5. For ease of rotation the coupling member 5 is provided with turning wings 30, 31. Radially opposite grooves 28, 29 in the bore 34 wall of the rotation restricting element 6 co-operate with radially opposite lugs 25, 25' disposed on a cylindrical portion 27 of the coupling member 5 so as to restrict insertion of the coupling member to one rotational position, in which the valve member 4 is disposed so that the terminal portion 22 of the coupling member 5 can be inserted in the oblong recess 21 of the valve member 4. The coupling member 5 is inserted until the distal face of its terminal portion 22 abuts the bottom face 21' of the valve member recess 21. To allow rotation of the coupling member 5 in a fully inserted position the bore 34 comprises diametrically opposite disposed widened portions 32, 33 extending for about 90° in one circumferential direction from grooves 28, 29. The widened portions 32, 33 allow the lugs 25, 25' to be rotationally displaced over an angle β of about 90° until they abut shoulders 26, 26' radially narrowing and limiting the widened portions 32, 33 of the bore 34. The shoulders 26, 26' are disposed so as to stop rotation of the coupling member 5 at an open position of the valve 4, 16. In the open position of the valve 4, 16 the coupling member 5 cannot be withdrawn from the bore 34 since the lugs 25, 25' hinder withdrawal by abutting upper faces of the widened portions 32, 33 of the bore 34, said upper faces extending in a plane parallel with the proximal end face 20 of the valve member 4. The distal ends of the coupling member conduits 23, 24 are in communication with flexible tubes 37, 38 attached to them via a connector 36, which is only represented schematically in FIG. 6. At their proximal ends the tubes 37, 38 are connected to a dialysis apparatus or similar equipment (not shown).

The connection of a person's circulation to a dialysis apparatus is only temporary since the access device of the invention 1 is only used in intervals of a few days for a couple of hours. At the end of a dialysis session the coupling member 5 is exchanged for a protecting cap 39 reflecting the design of the distal portions 22, 27 of the coupling member 5 and comprising corresponding lugs 40, 40'. Upon removal of the coupling member 5 with the valve 4, 16 in a closed position the protecting cap 39 is inserted into the bore 34 of the rotation restricting element 6 with the lugs 40, 40' disposed in the grooves 28, 29. In an inserted position the distal face 39' of the cap 39 abuts the bottom face 16' of the second recess 21 thereby closing the proximal openings of the insert conduits 12, 13. Rotation of the cap 39 by 90° is accomplished by turning a screw driver or similar gear inserted into a transverse slot 42 in the distal face of the cap 39. By this rotation the cap 39 is disposed in a position in which it cannot be withdrawn and in which the valve 4, 16 is closed. Additional sealing is provided by a circumferential radial flange 41 of the cap 39 abutting the proximal end face 20 of the valve member 4.

For exchange of the venous catheter 43, 44 the cap 39 is brought back to the closed condition of the valve 4, 16 and withdrawn. Then the cover 7 is dismounted. Finally, the insert 3 with the valve member 4 and the venous catheter 43, 44 is withdrawn through the proximal opening 11' of the housing 2 and replaced by a new insert with valve member and catheter 3, 4, 43, 44. To protect the cover 7 from contamination and damage a shield (not shown) may be mounted on it.

Example 2

Second Embodiment of the Device of the Invention

The second embodiment (FIG. 11) of the venous or peritoneal access device of the invention relates to a device for venous infusion or peritoneal infusion as well as peritoneal sequential infusion and drainage in peritoneal dialysis. The device 101 for venous infusion or peritoneal infusion or infusion/drainage shares all functional elements with the device for hemodialysis 1 of EXAMPLE 1 except for that its catheter is a single lumen venous or peritoneal catheter 147, 148 and that one 13, 18, 24 of the two fluid passages 12, 17, 23 and 13, 18, 24 extending between the hemodialysis catheter 47, 48 and the coupling member 5 has been omitted. In contrast to the double-channel embodiment of Example 1, the device of Example 3 is a single-channel venous access device. It can be used, for instance, for infusion of aqueous solutions or suspensions comprising pharmaceuticals and/or nutrients and/or salts. Elements of same function in the single fluid passage venous or peritoneal access device 101 of Example 3 as in the double fluid passage hemodialysis access device 1 of Example 1 retain the reference numbers of the latter 1 preceded by "10". In the device of Example 3 non-modified elements 2, 6, 7, 39 and their substructures are shared with the device of Example 1 and therefore retain their reference numbers. When used for peritoneal dialysis, the catheter of the device of the invention is one specifically designed for peritoneal access having a blunt tip (not shown) since it need not be inserted into a blood vessel.

Correspondence of FIGS. (first embodiment/second embodiment): 1a/1a; 1b/1d; 1c/1c; 2a/9a; 2b/9b; 2c/9c; 2d/9d; 2e/9e; 2f/9f; 3a/3a; 3b/3b; 4a/4a; 4b/4b; 4c/4d; 5a/10a; 5b/10b; 5c/10c; 5d/5d; 6/11.

Example 3

Variety of the Housing of the Device According to the Invention

The third embodiment of the invention relates to a housing 102' variety, FIG. 7, which can be substituted for the housing 2, 102 of the first and second embodiment of the device of the invention. The lower portion of the housing 102' is provided with a number of slits 150 extending in a circumferential direction. Also provided are a number of through bores 151 arranged near the distal skirt of the housing 102'. The bores 151 are provided to allow attachment of the housing 102' to surrounding tissue by means of suture. On a circumferential proximal flat face are disposed four threaded bores 152 for mounting of a cover 107' (FIG. 8) by means of screws. The cover 107' comprises an integral rotation restricting element 106' of a design corresponding to that of element 6, 106 of the first and third embodiments. Reference numbers indicate: 135, a central bore; 128, 129, diametrically opposite, axially extending grooves in the bore 135 wall; 126, a shoulder limiting the rotation of a coupling member (not shown) inserted into the bore 135. Also provided are four circumferentially disposed through bores 153 in a flat distal circumferential face of the cover 107' for insertion of mounting screws. The bores 153 are superimposable on the threaded bores 152 of the housing 102'.

Materials. The housing 2; 102; 102' of the device 1, 101 of the invention is preferably made of a stiff material, in particular a metallic or ceramic biocompatible material, for instance titanium or zirconium oxide, suitable for tissue integration. The other components of the device 1, 101, except for the flexible tubing of the catheter and the tubes connecting the device (1, 101) with a dialysis apparatus, are preferably made of a stiff biocompatible material, such as polylactide or poly(lactide-co-glycolide) of high molecular weight or a polyurethane/polyurea material. Surfaces of the device (1, 101) in contact with blood are preferably made anticoagulant by chemical treatment, such as by heparinization.

What is claimed is:

1. An access device for venous or peritoneal access, comprising:
 a housing comprising a void having a distal opening and a proximal opening;
 a venous or peritoneal access portion attached to a first face of an insert at a proximal end of the venous or peritoneal access portion, wherein a proximal most outer face of the housing is coplanar with a second face of the insert;
 a cylindrical valve element mountable in a cylindrical recess in the second face of the insert;
 wherein, upon implantation of the housing, the distal opening is disposed so as to face soft tissue of the patient whereas the proximal opening is disposed exteriorly of the patient, and wherein the insert with the venous or peritoneal access portion attached to the insert is mountable in the housing by inserting the venous or peritoneal access portion foremost into the proximal opening, and making the venous or peritoneal access portion pass through the distal opening.

2. The access device of claim 1, wherein the cylindrical recess in the insert for mounting the cylindrical valve element is disposed in a distal face thereof exteriorly of the patient's body.

3. The access device of claim 2, wherein the cylindrical valve element comprises a non-cylindrical recess disposed in a proximal face thereof.

4. The access device of claim 3, wherein the device comprises an extracorporeal coupling member, the extracorporeal coupling member comprising a distal terminal portion mountable in the recess of the cylindrical valve element, the extracorporeal coupling member comprising first and second conduits designed to be brought, in a coupled position, into fluid communication with first and second conduits of the cylindrical valve element at the distal openings of the first and second conduits of the extracorporeal coupling member.

5. The access device of claim 4, wherein the extracorporeal coupling member is mountable and dismountable in a closed valve position only.

6. The access device of claim 1, wherein the insert housed in the void of the housing does not extend through the distal opening thereof.

7. A device for venous or peritoneal access, comprising:
 a housing for implantation into soft tissue, comprising a void having a distal opening and a proximal opening;
 an insert for insertion into the housing through the proximal opening, wherein a proximal most outer face of the housing is coplanar with a second face of the insert;
 a venous or peritoneal access portion mounted at a distal portion of the insert;
 a cylindrical valve member mounted in a cylindrical recess of a proximal portion of the insert;
 an extracorporeal coupling member of which a distal terminal portion is insertable into a recess disposed at a proximal face of the cylindrical valve member;
 one or two conduits extending from the venous or peritoneal access portion to the proximal end of the extracorporeal coupling member via the cylindrical valve member and the insert so as to provide fluid communication between the venous or peritoneal access portion and the extracorporeal coupling member;
 wherein said communication can be interrupted by rotation of the extracorporeal coupling member.

8. The device of claim 7, wherein the extracorporeal coupling member cannot be withdrawn from the recess in state of fluid communication between the venous or peritoneal access portion and the extracorporeal coupling member via said one or more conduits.

9. The device of claim 8, wherein withdrawal and insertion of the extracorporeal coupling member is controlled by insertion control means comprised by a rotation restricting element of the device.

10. The device of claim 9, wherein the rotation restricting element comprises one or more shoulders disposed in distal sections of a central bore of the rotation restricting element, the one or more shoulders co-operating with one or more lugs disposed on a cylindrical portion of the coupling member.

11. The device of claim 10, wherein the insertion control means comprises one or more groves extending axially in a wall of the central bore capable of co-operating with the one or more lugs of the coupling member.

12. A device for venous or peritoneal access, comprising:
a housing comprising a void;
an insert disposable in the void and removable from the void, the insert comprising a first conduit extending from a first distal face thereof disposed intra-corporeally to a bottom face of a recess in a second proximal outer face thereof disposed extra-corporeally, the faces including an angle a of about 90°, wherein a proximal most outer face of the housing is coplanar with the second proximal outer face of the insert;
a cylindrical valve member housed in the insert recess, the cylindrical valve member comprising a first valve conduit extending between a distal end face of the cylindrical valve member and a bottom face of an oblong radially extending recess in a proximal face of the cylindrical valve member;
a coupling member comprising a portion extending from its distal end and capable of being inserted into the valve member recess and of being withdrawn from the valve member recess, the coupling member comprising a first coupling conduit communicating, in an inserted position, with the first valve member conduit;
wherein the first valve member conduit is displaceable by a rotation of the cylindrical valve member about its cylinder axis from an open position in which it is in communication with the first insert conduit to a closed position in which it is not or vice versa by rotation of the coupling member.

13. The device of claim 12, the insert comprising a second conduit of about same extension as the first conduit disposed in parallel therewith; a second valve member conduit of same extension as the first valve member conduit and disposed in parallel therewith, wherein the second valve member conduit can be brought into communication with the second insert conduit by rotation of the valve member about its cylinder axis; the coupling member comprising a second coupling conduit being in communication with the second valve member conduit at an inserted position of the valve member.

14. The device of claim 12, wherein the insert comprises coupling means disposed at a conduit of the single lumen venous catheter first distal face for coupling with a single lumen venous catheter so as to establish communication of its conduit with the first insert conduit.

15. The device of claim 13, wherein the insert comprises coupling means disposed at its first distal face for coupling with a double lumen venous catheter so as to establish communication of the conduits of the double lumen venous catheter with the insert conduits.

16. The device of claim 12, comprising a means for restricting a rotation of the coupling member, the means comprising a rotation restricting element.

17. The device of claim 16, wherein the rotation restricting element comprises one or more shoulders disposed in distal sections of a central bore of the rotation restricting element, the one or more shoulders co-operating with one or more lugs disposed on a cylindrical portion of the coupling member.

18. The device of claim 16, comprising a means for controlling the insertion of the coupling member into the valve member recess so as to only permit insertion or withdrawal at a closed position of the valve member, wherein the insertion control means is comprised by the rotation restricting element.

19. The device of claim 18, wherein the insertion control means comprises one or more grove(s) extending axially in the wall of the central bore capable of co-operating with the lug(s) of the coupling member, and wherein full insertion of the coupling member is only possible when the valve member is in a closed position.

20. The device of claim 17, wherein the cylindrical section carrying the lugs extends from the distal terminal section in a proximal direction.

21. The device of claim 16, wherein the rotation restricting element is comprised by a cover mountable on and dismountable from the proximal extracorporeal face of the housing.

* * * * *